United States Patent
Burkhardt et al.

(10) Patent No.: US 10,695,079 B2
(45) Date of Patent: Jun. 30, 2020

(54) THERAPY SYSTEM

(71) Applicant: RICHARD WOLF GMBH, Knittlingen (DE)

(72) Inventors: Michael Burkhardt, Mühlacker (DE); Francesco Messina, Kraichtal (DE); Jean-Georges Zimmermann, Knittlingen (DE)

(73) Assignee: RICHARD WOLF GMBH, Knittlingen (DE)

( * ) Notice: Subject to any disclaimer, the term of this patent is extended or adjusted under 35 U.S.C. 154(b) by 1146 days.

(21) Appl. No.: 14/775,163

(22) PCT Filed: Mar. 10, 2014

(86) PCT No.: PCT/EP2014/054580
§ 371 (c)(1),
(2) Date: Sep. 11, 2015

(87) PCT Pub. No.: WO2014/139950
PCT Pub. Date: Sep. 18, 2014

(65) Prior Publication Data
US 2016/0038166 A1   Feb. 11, 2016

(30) Foreign Application Priority Data
Mar. 14, 2013  (DE) .................. 10 2013 204 493

(51) Int. Cl.
*A61B 8/00* (2006.01)
*A61B 17/225* (2006.01)
(Continued)

(52) U.S. Cl.
CPC ........ *A61B 17/2255* (2013.01); *A61B 6/0457* (2013.01); *A61B 8/08* (2013.01);
(Continued)

(58) Field of Classification Search
None
See application file for complete search history.

(56) References Cited

U.S. PATENT DOCUMENTS 4,637,040 A * 1/1987 Sohval .................. A61B 6/032
378/10
5,044,354 A   9/1991 Goldhorn et al.
(Continued)

FOREIGN PATENT DOCUMENTS

DE   34 26 398 C1   11/1987
DE   36 38 953 A1   5/1988
(Continued)

*Primary Examiner* — Jonathan Cwern
(74) *Attorney, Agent, or Firm* — McGlew and Tuttle, P.C.

(57) ABSTRACT

A therapy system includes a therapy source (2) emitting radiation or waves, an ultrasound probe (14), a patient rest as well as a multi-axis positioning system (X, Y, Z) with several drives, by way of which the patient rest and the therapy source (2) can be moved to one another in all three spatial directions. A control device (26) is coupled to the ultrasound probe (14) and configured such that in at least one operating mode, the control device (26) simultaneously activates the drives of the multi-axis positioning system (X, Y, Z) such that the patient rest is moved relative to the therapy source along a selectable movement path (B) which lies within the plane of an ultrasound picture (20) which is currently recorded by the ultrasound probe (14). A method for positioning a patient rest relative to a therapy source is also provided.

20 Claims, 3 Drawing Sheets

(51) Int. Cl.
*A61B 6/04* (2006.01)
*A61B 8/08* (2006.01)

(52) U.S. Cl.
CPC .......... *A61B 8/085* (2013.01); *A61B 17/2256* (2013.01); *A61B 17/2251* (2013.01); *A61B 17/2258* (2013.01)

(56) References Cited

U.S. PATENT DOCUMENTS

| | | |
|---|---|---|
| 5,081,984 A | 1/1992 | Wess et al. |
| 5,350,351 A | 9/1994 | Saffer |
| 2003/0078523 A1* | 4/2003 | Burkhardt ............ A61B 6/4405 601/2 |
| 2003/0149352 A1 | 8/2003 | Liang et al. |
| 2008/0146908 A1 | 6/2008 | Wu |
| 2011/0082395 A1* | 4/2011 | Burkhardt .......... A61B 17/2255 601/2 |
| 2011/0166450 A1 | 7/2011 | Peyrard et al. |

FOREIGN PATENT DOCUMENTS

| | | |
|---|---|---|
| DE | 88 00 985 U1 | 8/1988 |
| DE | 42 11 274 C1 | 4/1993 |
| DE | 43 29 167 A1 | 3/1995 |
| EP | 0 269 801 A1 | 6/1988 |
| EP | 0 405 282 A1 | 1/1991 |
| EP | 2 308 398 A1 | 4/2011 |
| WO | 2011/061645 A1 | 5/2011 |

\* cited by examiner

THERAPY SYSTEM

CROSS REFERENCE TO RELATED APPLICATIONS

This application is a United States National Phase Application of International Application PCT/EP2014/054580 filed Mar. 10, 2014 and claims the benefit of priority under 35 U.S.C. §119 of German Patent Application 10 2013 204 493.3 filed Mar. 14, 2013 the entire contents of which are incorporated herein by reference.

FIELD OF THE INVENTION

The invention relates to a therapy system with a therapy source emitting radiation or waves, at least one ultrasound probe, a patient rest as well as a multi-axis positioning system (X, Y, Z) with several drives, by way of which the patient rest and the therapy source can be moved relative to one another in all three spatial directions, as well as to a method for positioning a patient rest relative to a therapy head of such a therapy system.

BACKGROUND OF THE INVENTION

With shock waves and ultrasound therapy systems, in particular lithotripters, it is necessary to position the focus of the therapy source to the patient in a defined manner. For this, it is known to lay the patient onto a movable patient rest which can be moved in three spatial coordinates relative to the therapy source. Thereby, it is known to carry out the positioning amid the aid of X-ray pictures or ultrasound pictures. Such a device is known for example from EP 2 308 398 A1.

From this document, it is already known to arrange positioning keys or buttons on the picture representation of the ultrasound or X-ray picture, and these permit the displacement of the patient such that the therapy focus is moved in the picture. The disadvantage with these arrangements is the fact that it often occurs that the physician loses sight of the point to be treated, for example a stone, from the recorded ultrasound picture, on account of the displacement movement along the three spatial coordinates and being necessary for positioning. This renders the positioning quite difficult.

SUMMARY OF THE INVENTION

It is therefore an object of the invention, to improve such a therapy system in a manner such that a simple and secure positioning of the therapy source relative to the patient is possible amid the aid of an ultrasound picture. This object is achieved by a therapy system with the therapy system features according to the invention as well as by a method with the method features according to the invention. Preferred embodiments are to be deduced from the depended claims, the subsequent description as well as the attached figures.

The therapy system according to the invention comprises a therapy source which emits radiation or waves. This, in particular, can be a therapy source which emits ultrasound or shock waves, i.e. a shock wave transducer for example. The therapy system according to the invention moreover comprises an ultrasound probe, with the help of which points in the patient body which are to be treated, for example stones such as kidney stones or gall stones, can be located. A patient rest is moreover provided. The therapy system is provided with a multi-axis positioning system with several drives, with the help of which the patient rest can be positioned relative to the therapy source in all three spatial directions. The patient rest and/or the therapy source are movable by way of positioning system for this.

According to the invention, the therapy system comprises a control device which is coupled to an ultrasound probe. Thereby, the coupling in particular is designed such that the control device detects the spatial position of the ultrasound picture. The control device according to the invention is moreover designed such that in at least one operating mode it simultaneously activates the drives, i.e. together, such that the patient rest is moved relative to the therapy source along a selectable movement path which lies within the plane of an ultrasound picture currently (presently) recorded by the ultrasound probe. This means that the drives are displaced such that a resulting movement direction of the patient rest relative to the therapy source is produced, and this is situated precisely in the picture plane or section plane of the ultrasound picture. I.e. here, the drives for the individual spatial directions are not moved successively in a separate manner and independently, as is the case with conventional systems known from the state of the art, but the displacement movement is effected simultaneously in all spatial directions, so that a resulting movement path is created, which lies in the plane of the ultrasound picture during the complete movement. For this, the control device takes the angle and the spatial position of the ultrasound picture into account. Thus, by way of such a system which does not realise a displacement movement in Cartesian coordinates, but along vectors, it is ensured that the therapy point to be treated, for example a stone, is not displaced out of the picture plane of the ultrasound picture on moving the patient relative to the therapy source.

The multi-axis positioning system can either by integrated completely into the patient rest or into the therapy source, i.e. either the patient rest alone is moved, or only the therapy source is moved. Alternatively, it is also possible to design both elements is a movable manner, wherein the movement axes of the therapy source and of the patient rest are then selected or complement one another such that a relative movement of the patient rest to the therapy source can be realized together in all three spatial directions.

The control device is designed such that according to the invention, it permits the previously outlined operation at least in one operating mode. This means that yet further operating modes for example permitting a displacement of the patient rest relative to the therapy source in the three spatial coordinates independently of one another can be provided in the control device.

The control device is preferably designed in a manner such that in the mentioned at least one operating mode, it activates the drives such that these displace simultaneously with speeds which are defined individually by the control device. This means that the drives do not need to be driven with the same displacement speeds with the simultaneous operation of these. In contrast, the displacement speeds are defined by the control device such that the displacement movement is achieved along the desired movement path in the picture plane, i.e. the current picture plane of the ultrasound picture. A displacement movement along a defined direction or line in the ultrasound picture is therefore achieved, wherein a control in the ultrasound picture is possible in real-time, and it is ensured that a therapy point which has been found for the first time, usually a stone, remains in the ultrasound picture the whole time during the movement.

Further preferably, the control device is designed in a manner such that the speeds with which the drives are displaced, are specified by the control device in a manner such that the ratio of the displacement speeds to one another corresponds to the ratio of the distances which are to be covered by the drives for displacement along the movement path. I.e., preferably the movement path according to the direction of the displacement movement is fixed in the ultrasound picture. In the case of a straight movement, a movement vector is thus defined in the ultrasound picture. When transformed onto the three spatial coordinates of the multi-axis positioning system, certain distances to be covered result for all drives, i.e. each coordinate axis with a drive. The displacement speed for the individual drives is defined by the control device on the basis of these distances to be covered. I.e. the drives which have to cover a further distance than others are accordingly moved more rapidly. The ratio of the distances to be covered, to one another, results from the respective gradient of the movement path to the coordinate axes.

Usefully, the control device is designed in a manner such that a vector can be selected in the ultrasound picture as a movement path, as has been described previously. I.e. a straight movement path is selected in the ultrasound picture or specified by way of the ultrasound picture. This for example can be accomplished by way of suitable actuation buttons on a display device for the ultrasound picture.

Further preferably, three drives which permit a movement along three axes perpendicular to one another are provided for the multi-axis positioning system, in the therapy system according to the invention. These axes thus correspond to the three Cartesian spatial coordinates. Thus, the patient rest can be displaced up and down as well as forwards and backwards in the longitudinal direction, and laterally to this in the transverse direction. What is thereby essential to the invention is the fact that all three drives are always simultaneously activated by the control device such that their speeds and distance are selected such that the displacement movement is effected along a movement path or vector, which is situated in the picture plane of the ultrasound picture. It is only when the picture plane of the ultrasound picture extends in only two of the three spatial coordinates that a displacement movement of only two associated drives is necessary, whereas the third drive is not driven.

The ultrasound probe is preferably integrated into the therapy source in a manner such that a therapy focus of the therapy source is situated in the ultrasound picture recorded by the ultrasound probe. The therapy focus thereby is further preferably characterized in the ultrasound picture, for example by way of crosshairs. The patient can be moved with the patient rest relative to the therapy source by way of suitable movement keys on the display device of the ultrasound picture, so that a point in the ultrasound picture and which is to be treated, for example a stone can be brought to coincide with the crosshairs. The drives of the multi-axis positioning system are thereby then simultaneously displaced such that the patient rest is moved relative to the therapy source such that it follows the movement path of the coordinate cross in the ultrasound picture in its picture plane. I.e. the located point to be treated, such as a stone, remains in the ultrasound picture during the complete movement. Thus, the characterized therapy focus can be moved relatively simply to a point to be treated.

The ultrasound source is further preferably rotatable relative to the therapy source, about an axis extending through the therapy focus, wherein a first angular measurement system which is connected to the control device and is for detecting the rotation angle between the ultrasound probes and the therapy source is present. The section picture, i.e. the recorded ultrasound picture is rotated about this axis by way of rotating the ultrasound probe. Thus, the point to be treated can be located in the ultrasound picture by way of rotation about this axis. Thereby, the spatial position, i.e. the angular position of the ultrasound picture about this axis is thereby detected by the first angular measurement system, so that the control device, in the case that a movement path is selected in this ultrasound picture, can spatially precisely determine this path whilst taking the angle into account, and in particular can assign it to the coordinate system of the multi-axis positioning system, i.e. the position of the ultrasound picture and thus of the movement path to be achieved can be transferred into the coordinate system of the multi-axis positioning system.

According to a further preferred embodiment, the therapy source is pivotable relative to the patient rest along an arcuate path, wherein a second angular measurement system which is connected to the control device and is for detecting the pivot angle between the therapy source and the patient rest is present. The pivotability along the arcuate path is preferably effected about a pivot axis which extends parallel to the longitudinal axis of the patient rest, i.e. parallel to the longitudinal axis of the patient lying on the patient rest. The ultrasound probe accordingly co-pivots about this arcuate path since it is preferably integrated into the therapy source. For this reason, the angular position of the ultrasound picture about this second pivot axis is made known to the control device by way of the second angular measurement system, so that with the knowledge of this angle, the defined movement path, in particular movement vector can continue to be transformed into the coordinate system of the multi-axis positioning system on defining a movement path in the ultrasound picture, and accordingly the movement can be effected precisely in the picture plane of the ultrasound picture, independently of the direction in which the ultrasound probe is pivoted. I.e. the control device according to the invention permits a displacement movement of the patient rest relative to the therapy source along a path which is situated in the ultrasound picture, independently of the current spatial position of the ultrasound picture.

Particularly preferably, the control device is designed in a manner such that in the at least one operating mode, it activates the drives in a manner such that a relative movement between the patient rest and the therapy source is possible exclusively along movement paths which are situated within the plane of the ultrasound picture. By way of this, one prevents the positioning of the patient and therapy source changing such that a desired therapy point, for example a stone, is moved out of the ultrasound picture. A faulty operation can thus be prevented, Further preferably, the control device is designed in a manner such that the movement path for a desired relative movement between the patient rest and the therapy source can be selected by the user within the plane of the current ultrasound picture. This can be effected for example by way of moving crosshairs characterising the therapy focus, in the ultrasound picture. Corresponding keys for activating a movement can alternatively be arranged on the screen or the display device for the ultrasound picture. It would also be conceivable, in the ultrasound picture, to define a direction or stretch, along which a displacement movement is to be effected, via a suitable input means, for example a computer mouse, a joystick or a pin.

Particularly preferably, keys for the selection of a movement direction defining the movement path are arranged on a screen representing the ultrasound picture or laterally of a screen representing the ultrasound picture. Thus, for example four keys corresponding to the movement directions up, down, right, left in the ultrasound picture can be provided. A movement of the patient rest relative to the therapy source can be initiated with such keys, so that a target point, e.g. a stone in the picture displaces such that it moves to the therapy focus, i.e. a movement to the selected position of the therapy focus along a straight stretch defining the movement path is effected. Such keys can be virtually faded into the picture of the screen when the screen is designed as a touch-sensitive screen.

The control device is usefully designed in a manner such that it transforms the spatial position of the selected path into the coordinate system of the multi-axis positioning system and then activates the drives such that a movement along the transformed path is effected. Thereby, the drives are simultaneously operated with speeds adapted in a defined manner, in the manner described above, so that the displacement movement is effected exactly along the path which is situated in the current, which is to say present picture plane of the ultrasound picture.

According to a particular embodiment of the invention, a membrane pressure control system can be provided, wherein this is designed in a manner such that it keeps constant a contact pressure of an outer surface of the therapy source which faces the patient, by way of pressure loading or pressure relief of a transmission path (forward path) formed in the therapy source. With shockwave transducers which can represent a therapy source, a fluid-filled transmission path is usually provided, which is closed to the patient by a membrane. It is necessary for the membrane to be held in a manner bearing on or in contact with the skin of the patient, in order to permit an adequate coupling of the shock waves into the body tissue of the patient. If the patient is now moved closer to the therapy apparatus or further away from it by way of the multi-axis positioning system or his own movement, then such a bearing contact or contact would possibly no longer be ensured. However, the transmission path is automatically lengthened or shortened by way of the membrane pressure control system, so that the membrane of the therapy head or of the therapy source is held with a defined bearing contact or contact on the skin of the patient. The membrane pressure control system for example can include a monitoring of the fluid pressure in the transmission path, so that this is kept constant or held in defined limits. The membrane pressure regulation system for this can be coupled to a pump which pumps additional fluid into the transmission path in a defined manner, or lets it out of the transmission path, in order to keep the pressure in the transmission path constant. The fluid in the transmission path is preferably water. Valves can be additionally or alternatively provided instead of a pump, and these are coupled to the control device, in order to be able to fill the transmission path with fluid in a defined manner or to discharge fluid in a defined manner, in order to keep the pressure constant in the inside. Accordingly, at least one pressure sensor is preferably present in the therapy source, and this can detect the pressure of the transmission path and be coupled to the control device.

The subject matter of the invention, apart from the described therapy system according to the invention, is a method for positioning a patient rest relative to a therapy source of a therapy system, for example a shock wave transducer. According to the method according to the invention, the therapy source is positioned by way of a current ultrasound picture. For this, a movement path, in particular a vector, along which the patient rest is to be displaced relative to the therapy source, is defined in the plane of the ultrasound picture, in the current ultrasound picture. The relative movement between the patient rest and the therapy source can thereby either be achieved alone by way of moving the patient rest or alone by way of moving the therapy source or however also by way of a common movement. Drives, by way of which the patient rest is movable relative to the therapy source are subsequently simultaneously driven such that a movement of the patient rest relative to the therapy head follows the defined movement path, i.e. the movement follows a movement path which is situated in the picture plane of the ultrasound picture. Thus, the movement at no point in time is effected out of the ultrasound picture, so that a therapy point, for example a stone, which has been firstly and once located in the ultrasound picture, remains in the ultrasound picture during the displacement movement and thus a control in real-time is possible. As described, the drives can move either the patient rest alone, the therapy source alone or however both, so that a relative movement is achieved. The previous description of the therapy system, from which the essential method features likewise result, is referred to with regard to the exact fashioning.

Usefully, the spatial position of the movement path, which is selected in the ultrasound picture, is transformed into a coordinate system of the movement axes along which the patient rest is moved relative to the therapy source, whilst taking into account the current spatial position of the plane of the ultrasound picture, and the drives are subsequently simultaneously activated such that a movement is effected along this transformed movement path. Thereby, movements in different directions, i.e. along different axes are not carried out successively but simultaneously, wherein the displacement speeds are usefully also set individually for the individual axes. Thus, the movement is effected along a movement path, in particular a vector, which is situated in the plane of the ultrasound picture.

For this, the displacement speeds of the individual drives are usually set such that their ratio to one another corresponds to the ratio of the distances to one another, said distances to be covered by the individual drives for displacement along the movement path. These distances (paths) correspond to the gradient of the vector which defines the movement path in the respective spatial direction of the coordinate system of the movement axes, along which the patient rest is moved relative to the therapy source. The drives, along whose axis farther or longer displacement distances are to be covered, accordingly are displaced more rapidly as a ratio.

The subject matter is hereinafter described by way of example and by way of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
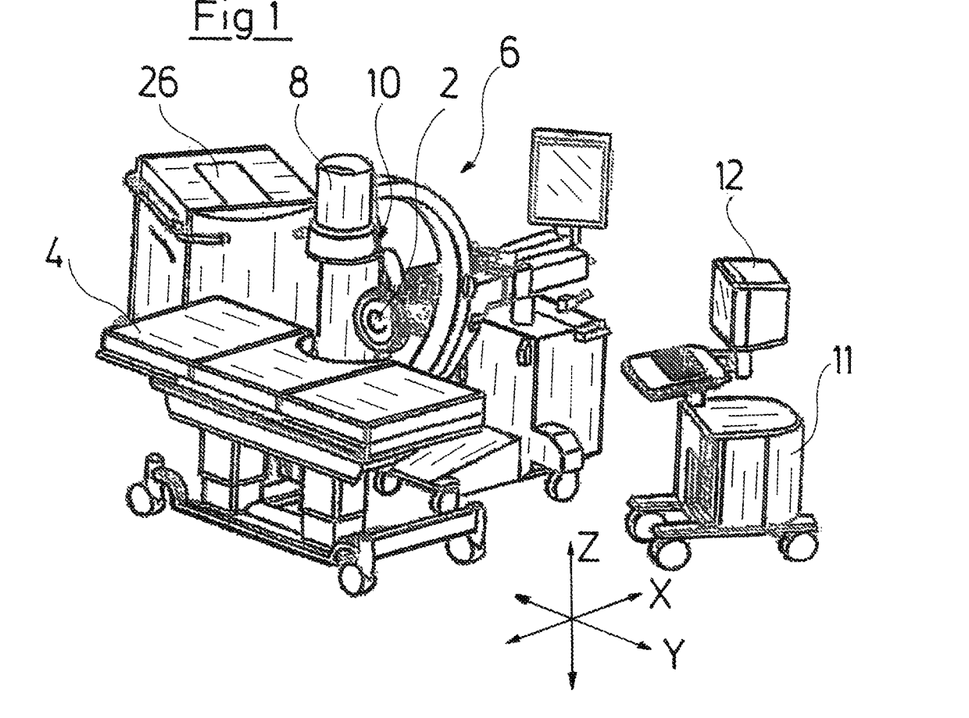
FIG. 1 is a schematic view of the complete arrangement of a therapy system according to the invention.

FIG. 1 by way of example shows a therapy system in the form of a lithotripsy device. This comprises a therapy source in the form of a shock wave transducer. A patient rest 4 is moreover provided, on which a patient to be treated comes to lie and which can be displaced and positioned relative to the therapy source 2. An X-ray C-arm 6 with any X-ray image intensifier 8 is moreover provided in this embodiment example. The therapy source 2 comprises an ultrasound probe which is not shown in detail in FIG. 1 and which is pivotable along an arcuate guide path 10 about an axis which extends parallel to the longitudinal axis of the patient rest and thus to the longitudinal axis of a patient on the patient rest 4. The ultrasound probe is connected to an ultrasound control apparatus 11 which comprises an ultrasound screen 12.

The patient rest 4 or its surface are displaceable relative to the therapy source 2 in spatial coordinates X, Y and Z which are at right angles to one another, in order to be able to position a patient on the patient rest 4 relative to the therapy source. For this, a multi-axis positioning system is provided, and this comprises three independent drives for realising the displacement movement along the axes X, Y and Z. The drives here are not shown in detail, and can be designed in the usual manner and are represented here by the axes X, Y and Z. With the embodiment example described here, the patient rest is envisaged to be displaced with the outlined drives in the direction of the three axes. However, it is to be understood that accordingly the therapy source 2 could also be displaced relative to the patient rest. It would also be conceivable to realise the relative movement by way of a superposition of movements of the patient rest 4 and the therapy source 2. The control of the drives is thereby effected according to the subsequent description.

Figure 2:
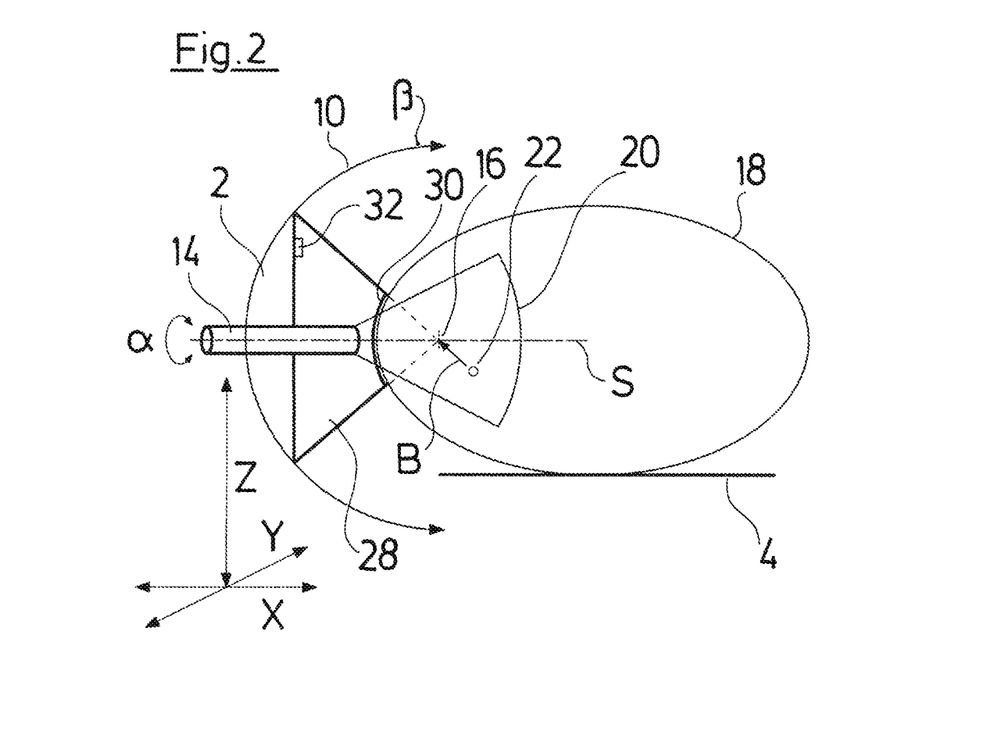
FIG. 2 is a schematic view of the positioning of the therapy source relative to an ultrasound picture.

As is schematically shown in FIG. 2, the complete therapy source 2 together with the ultrasound probe 14, which is arranged in it, is pivotable along an arcuate path 10 about the angle β. The ultrasound probe 14 is moreover rotatable within the therapy source 2 about an axis S about the angle α. The axis S thereby extends through the therapy focus 16 of the therapy source 2.

The patient 18 can be moved with the patient rest 4 in the X, Y and Z coordinates relative to the therapy source 2 via the drives. Suitable angle sensors are provided for positional detection of the therapy source 2 as well as the ultrasound source 14 about the pivot angles α and β. The ultrasound picture 20 which is recorded by the ultrasound probe 14 is a section picture through the body of the patient. The plane of the ultrasound picture 20 is thereby rotatable about the axis S and about the angle α. Moreover, it can pivot together with the therapy source 2 about the angle β along the arcuate path 10. A stone 22 which is distanced to the therapy focus 16 is schematically shown here in the ultrasound picture 20. It is thus necessary to move the patient 18 with the patient rest 4 such that the stone 22 comes to coincide with the therapy focus 16, for treating the stone. Since the ultrasound picture 20 can be rotated about the angle with respect to the axis S, the ultrasound picture 20 thereby does not necessarily extend in the plane which is spanned by the coordinate axes X and Z of the drives. Thus, a displacement movement of all three axes X, Y and Z is necessary as the case may be. Thereby, the difficulty arises of not losing the stone 22 from the ultrasound picture 20.

Figure 3:
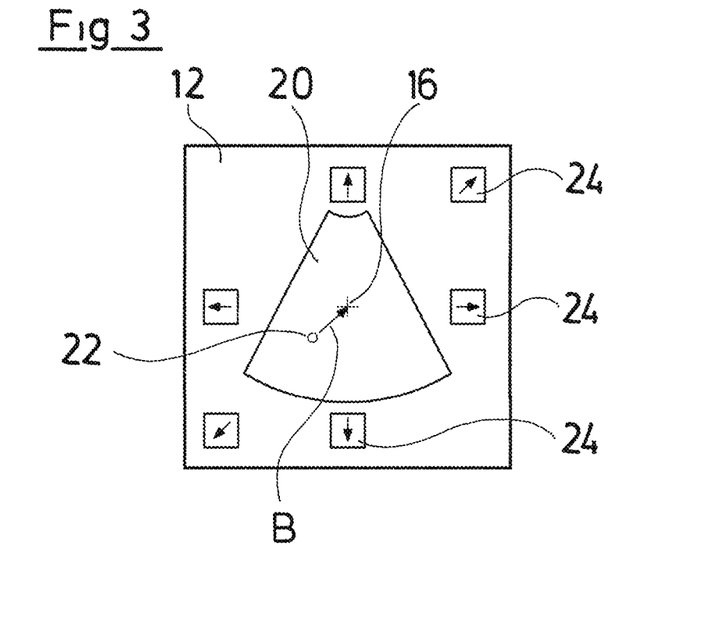
FIG. 3 is a schematic view of the ultrasound picture.
Figure 4:
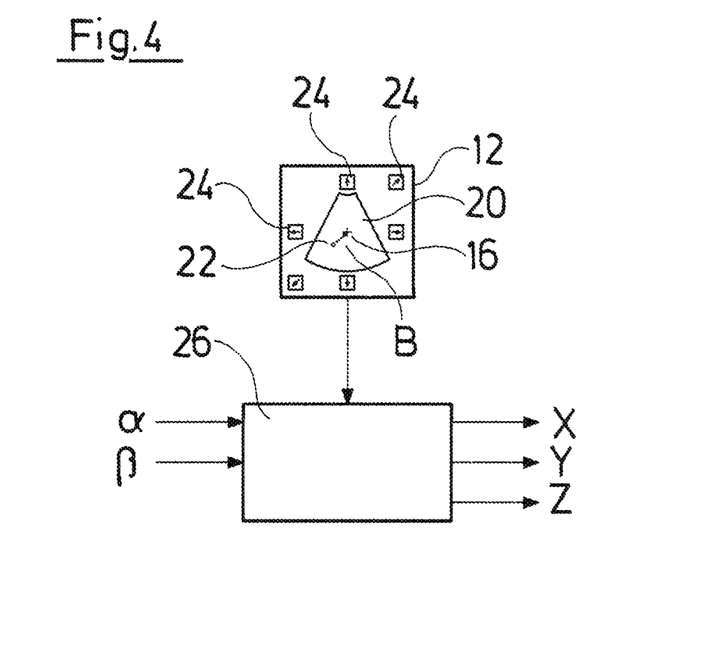
FIG. 4 is a schematic view of the transformation of the movement coordinates from of the ultrasound picture.

FIG. 3 by way of example shows the representation of the ultrasound picture 20 on the ultrasound screen 12. In this picture, the position of the therapy focus 16 is characterized, and the stone 22 can be recognized. Direction keys 24 as touch-sensitive fields are represented on the screen, with which keys a movement of the patient rest 4 can be initiated, so that the patient with the stone 22 can be displaced into the therapy focus 16. A movement path B in the form of a vector connecting the stone 22 and the therapy focus 16 in the ultrasound picture 20 is necessary for this. A displacement movement precisely in the current plane, i.e. the section plane of the ultrasound picture 20 is thus necessary. The necessary movements can be selected by the user at the ultrasound screen 12 by way of direction keys 24.

According to the invention, a control device 26 is now provided, and this is connected to the ultrasound control apparatus 11 and receives the commands of the direction keys 24. The control device 26 moreover receives the above mentioned angles α and β, about which the section plane of the ultrasound picture 20 is pivoted. The control device 26 receives the above mentioned angles α and β as input variables via suitable angle sensors. The control device 26, taking into account these angles, transforms the movement path or the movement vector B into the three spatial coordinates X, Y and Z of the drives of the patient rest 4. The drives X, Y and Z thereby obtain distance information with regard to the distance which the drives have to cover along the respective coordinate axis, as well as speed information which is adapted to these distances, from the control device 26. I.e., the control device 26 activates the drives of the axes X, Y and Z such that these are simultaneously displaced with adapted speeds. Thereby, the drive which has the greatest distance to cover is moved the quickest, and the drive which has to cover the shortest distance is driven the slowest. If for example the distance between the therapy focus 16 and the stone 22 along the Z-axis in the coordinate system of the patient rest 4 is three cm, along the Y-axis is two cm and along the X-axis is one cm, then the drive of the Z-axis is operated at triple the speed of the drive of the X-axis and the drive of the Y-axis is operated at double the speed of the drive of the X-axis. Thus, one succeeds in these three drives carrying out a resulting movement of the patient rest 4 precisely along the spatial direction of the movement vector B, along the axes X, Y and Z with a simulators drive. Thus, one succeeds in the patient being moved exactly in the plane of the ultrasound picture 20, and the stone 22 thus remaining in the ultrasound picture 20 during the complete movement, so that a visual control by the user is possible during the movement.

Figure 5:
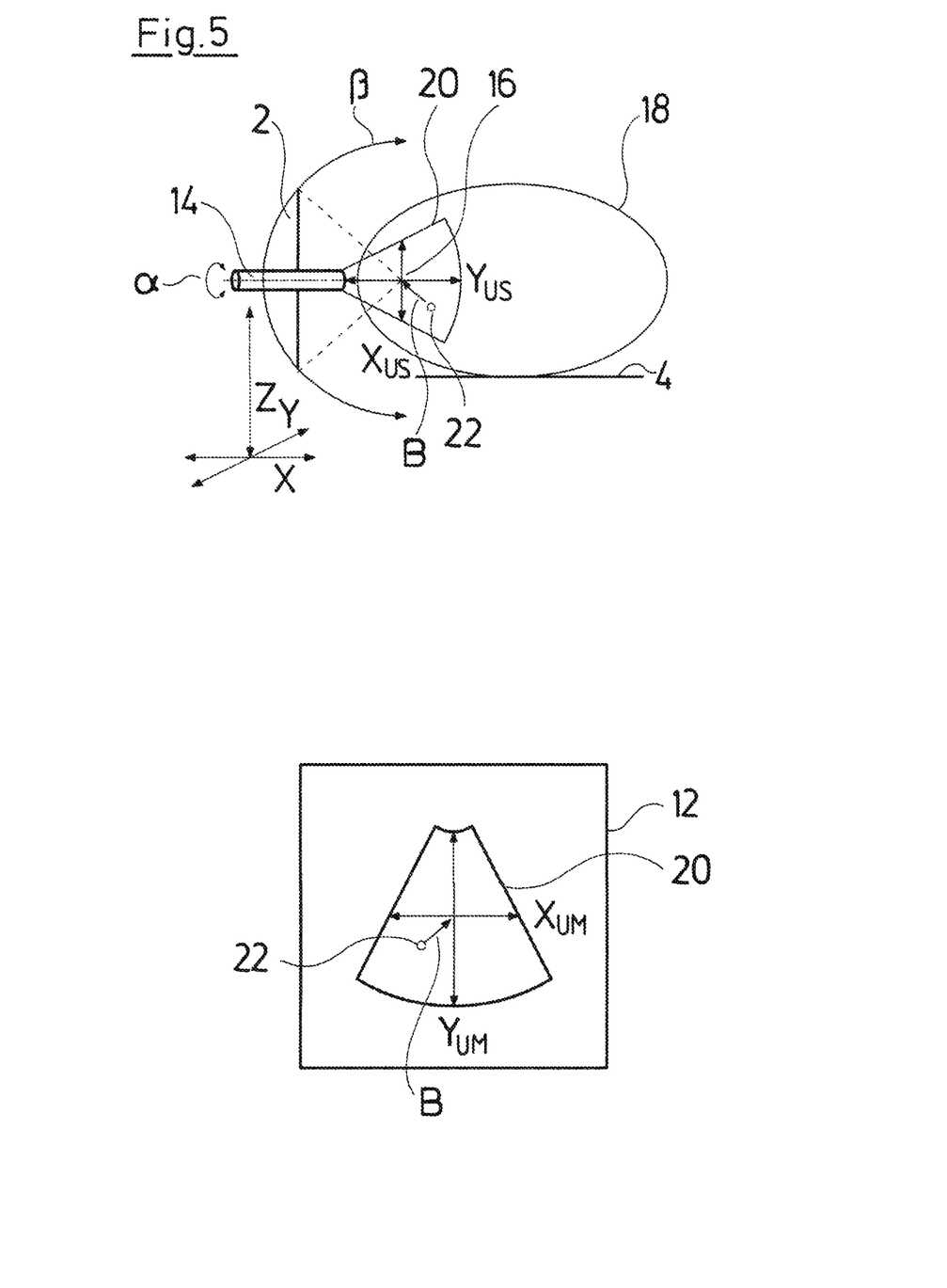
FIG. 5 is a schematic comparison of movement axes in the ultrasound picture and of the therapy source, relative to the patient rest.

As is to be recognized by way of FIG. 5, the $Y_{UM}$ coordinate in the two-dimensional ultrasound picture 20 on the ultrasound screen 12 extends in the same direction as the $Y_{US}$ axis of the ultrasound probe 14. Thereby, the ultrasound probe 14 is rotatable about the angle α about the $Y_{US}$ axis. The coordinate $Y_{UM}$ in the ultrasound picture 20 and which is at right angles to the $Y_{UM}$ coordinate always goes in the same direction as the $X_{US}$ axis of the ultrasound probe 14. The angles α and β are to be compensated in the control device 26 for the transformation of the movement vector B into the Cartesian coordinate system with the axes X, Y and Z of the patient rest 4. Thus, a first vector transformation, in which the angle α is compensated takes place. The angle β is compensated in a second vector transformation. The axis $Y_{US}$ of the ultrasound picture 20 extends parallel to the movement axis X of the patient rest, and the axis $X_{US}$ of the ultrasound probe 14 extends parallel to the axis Z of the coordinate system of the drives of the patient rest 4, if the ultrasound probe 14 is located in its middle position along the angle β and which is shown in FIG. 5 and it is located in the middle position shown in FIG. 5, in the direction of the pivot angle α. Thus, a movement direction in the Y-Z plane results from the transformation of the angle α into the coordinate system X, Y and Z, and a movement direction in the Z-X plane of this coordinate system results from the transformation of the angle β. Thus, movement coordinates for the drives in the coordinate system X, Y and Z of the patient rest 4 result from the position of the movement vector 22 along the axes $X_{US}$ and $Y_{US}$ together with the angles α and β. The drives are simultaneously displaced along the axes X, Y and Z with suitably adapted speeds, in order to then be able to move the patient rest 4 exactly along the vector 22.

It is to be understood that the therapy source 2 could also be moved along the axes X, Y and Z relative to the patient rest 4, instead of a movement of the patient rest 4. For example, it would also be conceivable to move the patient rest 4 along only one or two of the axes X, Y and Z, for example along the Y and X, whereas the therapy source is movable along the other axes, for example along the Z-axis. It is merely a question of the relative movement between the therapy source 2 and the patient rest 4 in the Cartesian coordinate system X, Y and Z.

The therapy source 2 is provided with a water-filled transmission path 28 which bears with a membrane 30 on the skin of the patient 18, in order to be able to couple the shock waves produced by the therapy source 2 into the body of the patient 18. If now the patient rest 4 is displaced along the axis X relative to the therapy source 2, then the patient 18 is thus moved away from the therapy source 2, and the membrane 30 would no longer lie in a surfaced manner on the surface of the body of the patient 18 as desired. A pressure control is provided in the transmission path 28, in order to compensate this. For this, a pressure sensor 32 which detects the pressure in the inside of the transmission path 28 is provided in the transmission path 28 or is coupled to this. Fluid can be led into the transmission path 28 or led out of this via suitable pumps or valves. By way of this, it is possible to keep the pressure in the inside of the transmission path 28 essentially constant. The control device 26 for this is preferably designed such that the pressure in the inside of the transmission path 28 is detected via the pressure sensor 32 after the therapy source 2 has been positioned with the transmission path 28 and the membrane 30 on the patient 18 in the desired manner, and then, with the movement of the patient 18 on the patient rest 4 relative to the therapy source 2, the pressure in the transmission path 28 is subsequently kept constant or is held within predefined limits, by way of fluid being led or pumped into the transmission path 28 as the case may be, or being let off in the case of a pressure which is too high. Thus, the bearing contact of the membrane 30 on the skin of the patient 18 can always be ensured in a defined manner, even with a movement of the patient 18, be it by way of displacing the patient rest 4 or due to the patient's own movements.

While specific embodiments of the invention have been shown and described in detail to illustrate the application of the principles of the invention, it will be understood that the invention may be embodied otherwise without departing from such principles.

The invention claimed is:

1. A therapy system comprising:
   a therapy source emitting radiation or waves;
   at least one ultrasound probe;
   a patient rest;
   a multi-axis positioning system with several drives, by way of which the patient rest and the therapy source are moved relative to one another in all three spatial directions; and
   a control device which is coupled to the ultrasound probe and configured to, in at least one operating mode, simultaneously activate the drives of the multi-axis positioning system in a manner such that the patient rest is moved relative to the therapy source along a selectable movement path based on input from a control user interface, wherein the selectable movement path lies within the plane of an ultrasound picture which is currently recorded by the ultrasound probe, the control device being configured such that the speeds, with which the drives are displaced, are specified by the control device in a manner such that the ratio of the displacement speeds to one another corresponds to the ratio of the distances which are to be covered by the drives for displacing along the movement path.

2. A therapy system according to claim 1, wherein the control device is configured such that in the at least one operating mode, the control device activates the drives such that these can be displaced simultaneously with speeds defined individually by the control device, wherein one of the drives is moved at a faster speed to cover a greater distance than another one of the drives that is moved to cover a lesser distance.

3. A therapy system according to claim 1, wherein the control device is configured such that a vector can be selected in the ultrasound picture as a movement path.

4. A therapy system according to claim 1, wherein the several drives comprise three drives that permit a movement along three axes which are normal to one another.

5. A therapy system according to claim 1, wherein the ultrasound probe is integrated into the therapy source in a manner such that a therapy focus of the therapy source is situated in the ultrasound picture which is recorded by the ultrasound probe.

6. A therapy system according to claim 5, wherein the ultrasound probe is rotatable relative to the therapy source, about an axis extending through the therapy focus, wherein a first angular measurement system which is connected to the control device is present for detecting the rotation angle between the ultrasound probe and the therapy source.

7. A therapy system according to claim 6, wherein the therapy source is pivotable relative to the patient rest along an arcuate path, wherein a second angular measurement system which is connected to the control device is present for detecting the pivot angle between the therapy source and the patient rest.

8. A therapy system according to claim 1, wherein the control device is configured such that in the at least one operating mode, the control device activates the drives in a manner such that a relative moment between the patient rest and the therapy source is possible exclusively along movement paths which are situated within the plane of the ultrasound picture.

9. A therapy system according to claim 1, wherein the control device is configured such that the movement path for a desired relative movement between the patient rest and the therapy source within the plane of the current ultrasound picture can be selected by the user.

10. A therapy system according to claim 9, wherein the control user interface comprises keys for the selection of a movement direction defining the movement path are arranged on a screen representing the ultrasound picture or laterally of a screen representing the ultrasound picture.

11. A therapy system according to claim 9, wherein the control device is configured such that the control device transforms the spatial position of the selected path into the coordinate system of the multi-axis positioning system, and activates the drives in a manner such that a movement along the transformed path is effected.

12. A therapy system according to claim 1, further comprising a membrane pressure control system which is configured such that the membrane pressure control system keeps constant a contact pressure of an outer surface of the therapy source which faces the patient, by way of pressure subjection or pressure relief of a transmission path formed in the therapy source.

13. A method for positioning a patient rest relative to a therapy source by way of a current ultrasound picture, the method comprising the steps of:
defining a movement path, along which the patient rest is to be displaced relative to the therapy source in the current ultrasound picture in the plane of the ultrasound picture detected via an ultrasound probe;
providing drives, by way of which the patient rest can be moved relative to the therapy source;
driving the drives simultaneously based on input from a user control interface such that a movement of the patient rest relative to the therapy source follows the defined movement path, wherein the displacement speeds of the individual drives are set such that their ratio to one another corresponds to the ratio to one another of the distances which are to be covered by the individual drives for displacing along the movement path.

14. A method according to claim 13, wherein the movement path is a vector, wherein one of the drives is moved at a faster speed to cover a greater distance than another one of the drives that is moved to cover a lesser distance.

15. A method according to claim 13, wherein the spatial position of the movement path is transformed into a coordinate system of the movement axes, along which the patient rest is moved relative to the therapy source, whilst taking into account the current spatial position of the plane of the ultrasound picture, and subsequently the drives are simultaneously activated such that a movement is effected along this transformed movement path.

16. A therapy system comprising:
a therapy source emitting radiation or waves;
at least one ultrasound probe;
a user control interface;
a patient rest;
a multi-axis positioning system with several drives, by way of which the patient rest and the therapy source are moved relative to one another in all three spatial directions; and
a control device which is coupled to the ultrasound probe and configured to, in at least one operating mode, simultaneously activate the drives of the multi-axis positioning system based on input from the user control interface such that the patient rest is moved relative to the therapy source along a selectable movement path which lies within the plane of an ultrasound picture which is currently recorded by the ultrasound probe, the drives comprising a first drive configured to move the patient rest along a first axis, a second drive configured to move the patient rest along a second axis and a third drive configured to move the patient rest along a third axis, the first axis, the second axis and the third axis being different from one another, the control device synchronizing a speed of the first drive, a speed of the second drive and a speed of the third drive such that the patient rest moves along the first axis, the second axis and the third axis.

17. A therapy system according to claim 16, wherein the speed of the first drive, the speed of the second drive and the speed of the third drive are controlled by the control device such that a ratio of the speed of the first drive, the speed of the second drive and the speed of the third drive corresponds to a ratio of distances which are to be covered by the first drive, the second drive and the third drive for displacing the patient rest along the movement path, wherein at least one of the first drive, the second drive and the third drive is moved at a first speed to cover a first distance and at least another one of the first drive, the second drive and the third drive is moved at a second speed to cover a second distance, the first speed being greater than the second speed, the first distance being greater than the second distance.

18. A therapy system according to claim 16, wherein the control device is configured such that a vector can be selected in the ultrasound picture as a movement path.

19. A therapy system according to claim 16, wherein the first axis, the second axis and the third axis are perpendicular to one another.

20. A therapy system according to claim 16, wherein the ultrasound probe is integrated into the therapy source in a manner such that a therapy focus of the therapy source is situated in the ultrasound picture which is recorded by the ultrasound probe.

* * * * *